US012728010B2

(12) United States Patent
Walkington

(10) Patent No.: US 12,728,010 B2
(45) Date of Patent: Sep. 8, 2026

(54) KNEE PROSTHESIS HAVING NON-UNIFORM STIFFNESS

(71) Applicant: DEPUY IRELAND UNLIMITED COMPANY, Ringaskiddy (IE)

(72) Inventor: Mathew J. Walkington, West Yorkshire (GB)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 715 days.

(21) Appl. No.: 17/566,775

(22) Filed: Dec. 31, 2021

(65) Prior Publication Data

US 2023/0210670 A1 Jul. 6, 2023

(51) Int. Cl.
*A61F 2/38* (2006.01)
*A61F 2/30* (2006.01)

(52) U.S. Cl.
CPC .... *A61F 2/389* (2013.01); *A61F 2002/30014* (2013.01); *A61F 2002/30322* (2013.01);
(Continued)

(58) Field of Classification Search
CPC ............ A61F 2/389; A61F 2002/30014; A61F 2002/30006; A61F 2002/30322;
(Continued)

(56) References Cited

U.S. PATENT DOCUMENTS 5,282,861 A * 2/1994 Kaplan .................. B22F 3/114 623/23.51
7,578,851 B2 * 8/2009 Dong ..................... C23C 26/00 623/22.21

(Continued)

FOREIGN PATENT DOCUMENTS

CN 108742952 A 11/2018
CN 111449808 A 7/2020

(Continued)

OTHER PUBLICATIONS

Maskery et al., Effective design and stimulation of surface-based lattice structures featuring volume fraction and cell type grading, Materials and Design, 2018, p. 220-232 (Year: 2018).*

(Continued)

*Primary Examiner* — Yashita Sharma
*Assistant Examiner* — Kia Xiong White
(74) *Attorney, Agent, or Firm* — Barnes & Thornburg LLP

(57) ABSTRACT

A knee prosthesis comprises a unicondylar knee prosthesis having a unicondylar insert platform and a tibial base attached to a bottom side of the unicondylar insert platform. The unicondylar insert platform has a uniform stiffness gradient (e.g., a density or porosity gradient), whereas the tibial base has a non-uniform stiffness gradient (e.g., a density or porosity gradient) when the tibial base is viewed from a cross-sectional coronal plan. For example, the tibial base may have an area of greatest stiffness or density centrally located relative to an inboard and outboard side of the tibial base. Alternatively, the area of greatest stiffness or density may be located toward the outboard side. Additionally, the tibial base may include density wells having increased density relative to the surrounding area of the tibial base.

17 Claims, 10 Drawing Sheets

(52) U.S. Cl.
CPC ............... *A61F 2002/30878* (2013.01); *A61F 2002/3092* (2013.01); *A61F 2002/30952* (2013.01); *A61F 2310/00023* (2013.01)

(58) Field of Classification Search
CPC .... A61F 2002/30878; A61F 2002/3092; A61F 2310/00023; A61F 2/3094; A61F 2002/30011; A61F 2002/30985; A61F 2/3868
See application file for complete search history.

(56) References Cited

U.S. PATENT DOCUMENTS

| | | | | |
|---|---|---|---|---|
| 8,430,930 | B2 | 4/2013 | Hunt | |
| 2011/0202140 | A1* | 8/2011 | Turner | A61F 2/36 623/18.11 |
| 2014/0277548 | A1* | 9/2014 | Cohen | A61F 2/3859 623/20.34 |
| 2019/0298533 | A1* | 10/2019 | Kane | A61L 27/306 |

FOREIGN PATENT DOCUMENTS

| | | | | |
|---|---|---|---|---|
| CN | 112155796 | A | 1/2021 | |
| EP | 3388029 | A1 | 10/2018 | |
| WO | WO-2022153033 | A1 * | 7/2022 | A61F 2/32 |

OTHER PUBLICATIONS

Loon et al., "Periprosthetic Fracture of the Tibial Plateau After Unicompartmental Knee Arthroplasty," Acta Orthop. Belg., 2006, 72, 369-374, 6 pages.
Maskery et al., "Effective Design and Simulation of Surface-Based Lattice Structure Featuring Volume Fraction and Cell Type Grading," Materials and Design 155, 2018, 220-232, 16 pages.
Rho et al., "Young's Modulus of Trabecular and Cortical Bone Material: Ultrasonic and Microtensile Measurements," J. Biomechancis vol. 26, No. 2, pp. 111-119, 1993, 9 pages.
Murgatroyd, "Design & Analysis of 3D Printed Bone Like Structures for Orthopaedic Applications," Dept. of Engineering and Mathematics, Sheffield Hallam University, Jul. 23, 2020, 88 pages.
International Search Report for International Application No. PCT/GB2022/050016; Mar. 17, 2022; 42 pages.

* cited by examiner 100
102
500
502
104
134
132

100
102
412
402
602
604
606
104

100
102
412
402
602
604
606
104

100
102
412
402
602
604
606
104

100
102
412
402
602
604
606
104

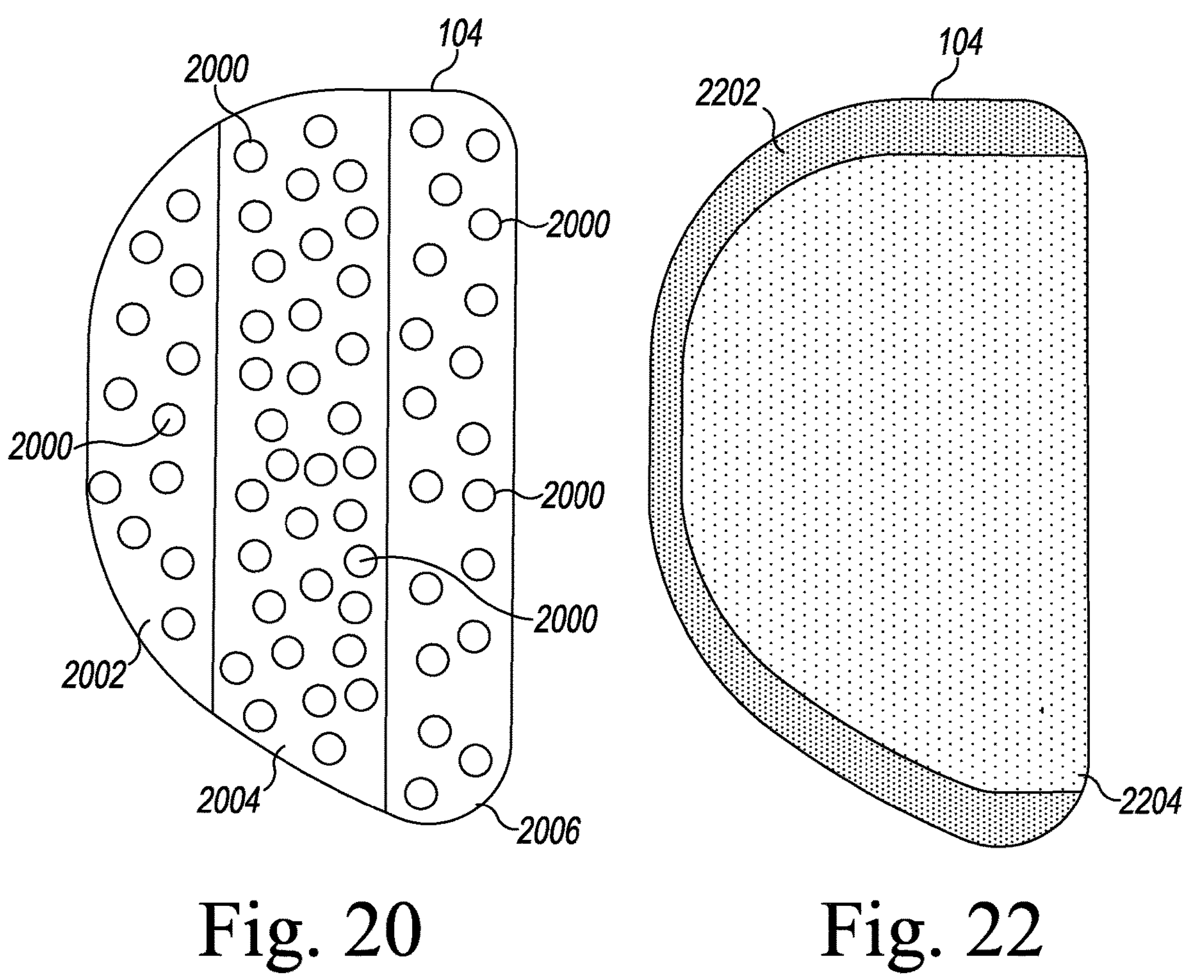
Fig. 20
Fig. 22
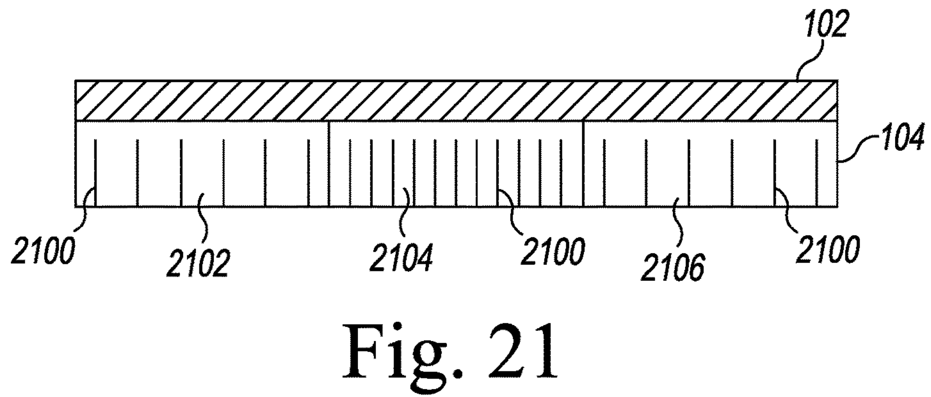
Fig. 21

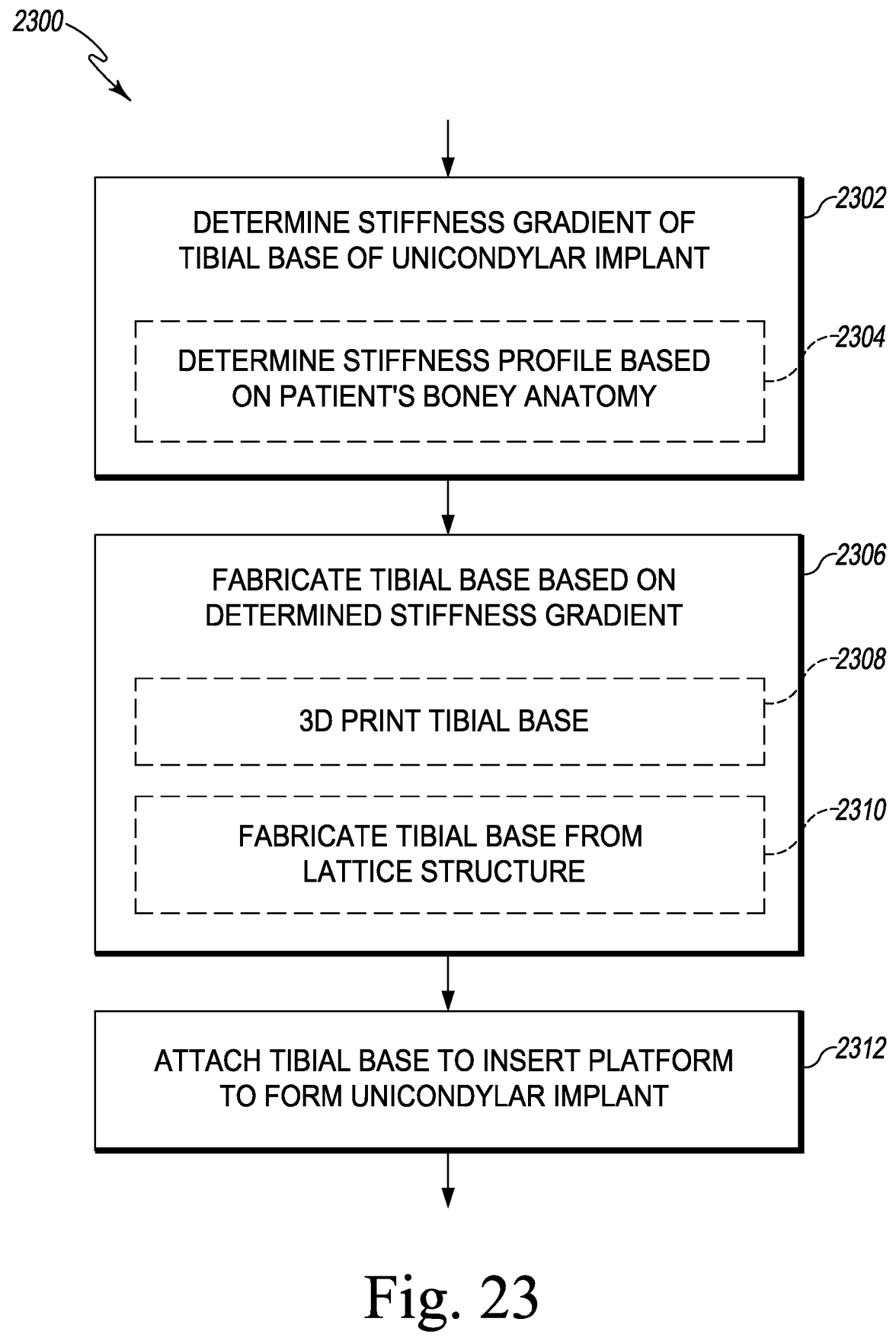

2300

DETERMINE STIFFNESS GRADIENT OF TIBIAL BASE OF UNICONDYLAR IMPLANT — 2302

DETERMINE STIFFNESS PROFILE BASED ON PATIENT'S BONEY ANATOMY — 2304

FABRICATE TIBIAL BASE BASED ON DETERMINED STIFFNESS GRADIENT — 2306

3D PRINT TIBIAL BASE — 2308

FABRICATE TIBIAL BASE FROM LATTICE STRUCTURE — 2310

ATTACH TIBIAL BASE TO INSERT PLATFORM TO FORM UNICONDYLAR IMPLANT — 2312

Fig. 23

KNEE PROSTHESIS HAVING NON-UNIFORM STIFFNESS

TECHNICAL FIELD

The present disclosure relates generally to orthopaedic prostheses, and more particularly, to knee prostheses having non-uniform stiffness.

BACKGROUND

Joint arthroplasty is a well-known surgical procedure by which a diseased and/or damaged natural joint is replaced by a prosthetic joint. For example, in a knee arthroplasty surgical procedure, a patient's natural knee joint is partially or totally replaced by a prosthetic knee joint.

A total knee replacement or arthroplasty may involve replacement of the mid-shaft portion of the femur, proximal, distal, and/or total femur, and proximal tibia. Conversely, unicondylar knee replacement or arthroplasty involves unicondylar resurfacing. Unicondylar knee arthroplasty provides an alternative to total knee arthroplasty for rehabilitating knees when only one condyle has been damaged as a result of trauma or disease such as noninflammatory degenerate joint disease or its composite diagnosis of osteoarthritis or post-traumatic arthritis, for example. As such, unicondylar knee arthroplasty may be indicated for use in patients undergoing surgery for a severely painful and/or disabled joint damaged as a result of osteoarthritis, traumatic arthritis, rheumatoid arthritis, or a failed previous implant when only one condyle of the knee (medial or lateral) is affected. Further, unicondylar knee replacements may be "multi-piece" replacements in which a separate unicondylar tibial insert is used to replace each of the medial and lateral condyles of the patient. A single, total femoral component or two partial femoral components may be used to cooperate with the two unicondylar inserts.

Unicondylar knee replacements are intended to provide increased patient mobility and reduce pain by replacing the damaged knee joint articulation in patients where there is evidence of sufficient sound bone to seat and support the components. Age and activity level factor into all reconstructive procedures and the state of the arthritis determines the treatment. With the advancement of minimally invasive techniques that support unicondylar knee reconstruction, a growing number of patients are offered this alternative for relief from the disabling pain of arthritis and for the potential benefits of a rapid recovery.

One consideration of joint arthroplasty is bone growth around or near the implanted knee prosthesis. Bone tissue growth and resorption is directly related to the loading experienced by the bone tissue. This phenomenon, which is referred to as Wolfe's law, results in abnormal growth of bone tissue that experiences abnormal loading. Abnormal growth of the bone tissue may be, for example, a result of stress shielding where the bone density is considerably lower in a region adjacent to an implant. The bone density lowers due to the implant experiencing the brunt of the load in the region, i.e., the implant shields the bone from stress, resulting in reduced density. The reduced density can weaken the bone tissue in the region to a point where there is an increased risk of further dysfunction or damage, such as fracturing.

One particular issue with orthopaedic implants in view of Wolfe's law is the geometric and material requirements. Orthopaedic implants, generally, comprise materials other than bone tissue, such as various metals and/or polymers. The materials may be chosen to match the material properties of native bone tissue as closely as possible, but a perfect match is difficult to achieve. Further, the shape of the implant must match the shape of the portion of bone that is resected to allow implantation. This is particularly important with regards to thicknesses of the implant in various regions, which may have a thickness that results in excessive stiffness in order to properly fill the joint space. These two issues can contribute to abnormal bone loading.

SUMMARY

According to an aspect of the present disclosure, a unicondylar knee prosthesis includes a unicondylar insert platform having a top surface configured to support a unicondylar tibial insert and a bottom surface opposite the top surface and a tibial base attached to the bottom surface of the bearing platform layer and extending distally therefrom. The unicondylar insert platform may have a substantially uniform stiffness (e.g., density) gradient, and the tibial base may have a non-uniform stiffness (e.g., density) gradient when viewed from a cross-sectional coronal plane.

In some embodiments, the unicondylar insert platform has a stiffness (e.g., density) that is greater than a stiffness (e.g., density) of any portion of the tibial base. Additionally or alternatively, in some embodiments, the unicondylar insert platform may be formed from a titanium material and the tibial base is formed from a Body-Centered Cubic (BCC) lattice structure.

Additionally, in some embodiments, the tibial base has an inboard side and an outboard side opposite the inboard side. The stiffness (e.g., density) gradient of the tibial base may be non-uniform in an inboard-outboard direction. Additionally, the tibial base may include an anterior side and a posterior side opposite the anterior side, and the stiffness (e.g., density) gradient of the tibial base may be non-uniform in an anterior-posterior direction. In some embodiments, the tibial base may be defined by multiple sections when viewed from the cross-sectional coronal plane. In such embodiments, each section may have a uniform stiffness (e.g., density) that is different from each other section. Additionally, in some embodiments, the multiple sections of the tibial base may include an inboard-most section and an outboard-most section. In such embodiments, the inboard-most section may have the least stiffness (e.g., density) of the multiple sections and the outboard-most section may have the greatest stiffness (e.g., density) of the multiple sections. Alternatively, in some embodiments, the multiple sections of the tibial base may include a central section, a first section adjacent to the central section on an inboard side of the central section, and a second section adjacent to the central section on an outboard side of the central section. In such embodiments, the central section may have a stiffness (e.g., density) that is greater than either the first or second sections.

In some embodiments, the stiffness gradient of the tibial base is embodied as a density gradient that may increase in density from a low density area located toward the inboard side of the tibial base to a high density area, relative to the low density area, located toward the outboard side of the tibial base. Alternatively, in some embodiments, the density gradient of the tibial base may have a central area located between the inboard side and the outboard side of the tibial base and having the greatest density relative to other areas of the tibial base. Additionally or alternatively, the density gradient of the tibial base may also non-uniform in a proximal-distal direction.

Additionally, in some embodiments, the tibial base comprises a density well. The density well may define a volume of the tibial base having an increased density relative to a region of the tibial base adjacent to the density well. Additionally, the density well may have a non-uniform density gradient in an inboard-outboard direction and a proximal-distal direction. Furthermore, the density well may be defined by an outer edge adjacent the region of the tibial base. The outer edge may be non-linear when the tibial base is viewed from the cross-sectional coronal plane.

According to another aspect of the present disclosure, a unicondylar knee prosthesis may include a polymer unicondylar tibial insert and a unicondylar tibial tray. The unicondylar tibial tray may include a unicondylar insert platform and a tibial base. The unicondylar insert platform may have a top surface configured to support the polymer unicondylar tibial insert and a bottom surface opposite the top surface. Additionally, the unicondylar insert platform may be formed from a titanium material and have a substantially uniform stiffness (e.g., density) gradient. The tibial base may be attached to the bottom surface of the unicondylar insert platform and extend distally therefrom. Additionally, the tibial base may be formed from a Body-Centered Cubic (BCC) lattice structure and have an inboard side and an outboard side opposite the inboard side. The tibial base may have a stiffness (e.g., density) gradient that is non-uniform in the inboard-outboard direction when viewed from a cross-sectional coronal plane.

In some embodiments, the tibial base may further include a plurality of density wells spatially separated from each other. Each density well may define a volume of the tibial base having an increased density relative to a region of the tibial base adjacent to the corresponding density well.

According to yet another aspect of the present disclosure, a method for fabricating a unicondylar knee prosthesis may include determining a non-uniform stiffness (e.g., density) gradient for a tibial base of the unicondylar knee prosthesis, fabricating the tibial base based on the determined non-uniform stiffness (e.g., density) gradient; and attaching the fabricated tibial base to a bottom surface of a unicondylar insert platform to form the unicondylar knee prosthesis. The non-uniform stiffness (e.g., density) gradient may define a variation in stiffness (e.g., density) of the tibial base from an inboard side of the tibial base to an outboard side of the tibial base when viewed from a cross-sectional coronal plane. Additionally, the unicondylar insert platform may include a top surface configured to support a unicondylar tibial insert and have a substantially uniform stiffness (e.g., density) gradient.

In some embodiments, fabricating the tibial base may include fabricating a Body-Centered Cubic (BCC) lattice structure having the determined non-uniform stiffness (e.g., density) gradient. Additionally, in some embodiments, determining the non-uniform stiffness (e.g., density) gradient may include determining a non-uniform stiffness (e.g., density) gradient for the tibial base that increases in stiffness (e.g., density) from a low stiffness (e.g., density) area located toward the inboard side of the tibial base to a high stiffness (e.g., density) area, relative to the low stiffness (e.g., density) area, located toward the outboard side of the tibial base. Additionally or alternatively, in some embodiments, determining the non-uniform stiffness (e.g., density) gradient may include determining a non-uniform stiffness (e.g., density) gradient for the tibial base that has an area of greatest stiffness (e.g., density) that is centrally located between the inboard side and the outboard side of the tibial base.

BRIEF DESCRIPTION OF THE DRAWINGS

The detailed description particularly refers to the following figures, in which:

FIG. 20 is a bottom plan view of another embodiment of the unicondylar knee prosthesis of FIGS. 1-5 including a tibial base having a non-uniform stiffness gradient formed from distinct sections having a varying number of apertures formed therein;

FIG. 21 is a coronal cross-sectional elevation view of another embodiment of the unicondylar knee prosthesis of FIG. 5 including a tibial base having a non-uniform stiffness gradient formed from distinct sections having a varying number of slots formed therein;

FIG. 22 is a top plan view of another embodiment of the unicondylar knee prosthesis of FIGS. 1-5 having an outboard rim of higher density;

FIG. 23 is a flow chart diagram of an embodiment of a method for fabricating a unicondylar knee prosthesis.

DETAILED DESCRIPTION OF THE DRAWINGS

Figure 1:
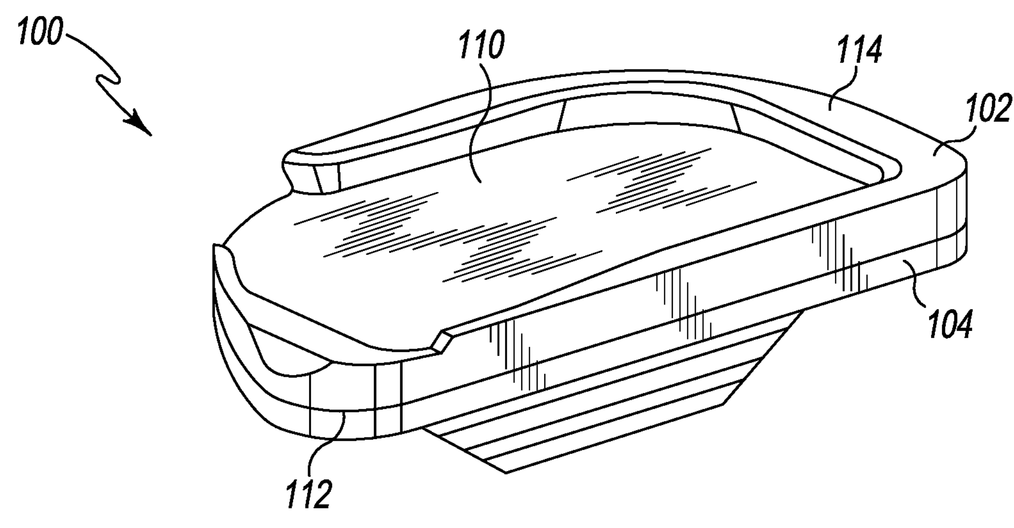
FIG. 1 is a perspective view of an embodiment of a unicondylar knee prosthesis having a unicondylar insert platform and a tibial base attached to a bottom surface of the unicondylar insert platform.
Figure 2:
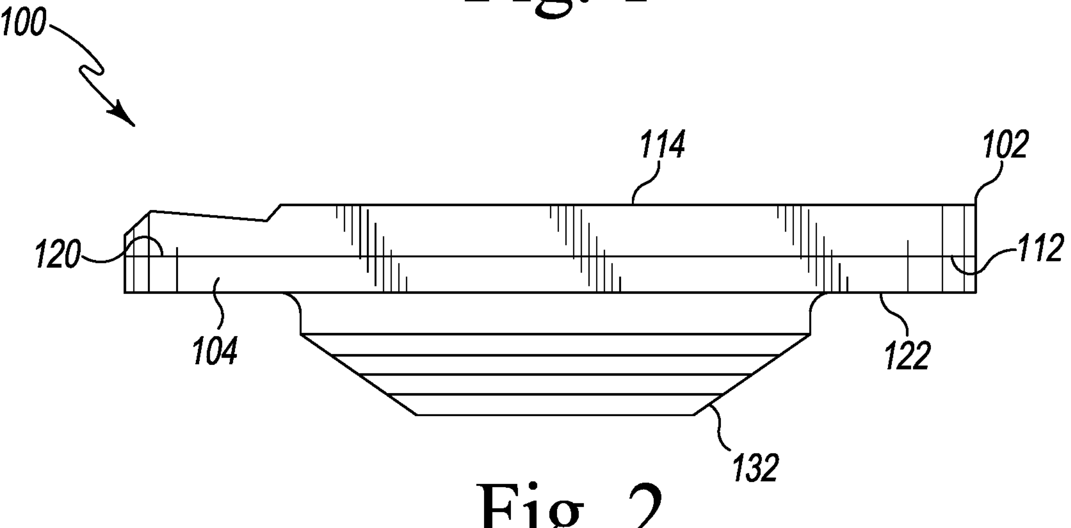
FIG. 2 is an inboard side elevation view of the unicondylar knee prosthesis of FIG. 1.

While the concepts of the present disclosure are susceptible to various modifications and alternative forms, specific illustrative embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Figure 24:
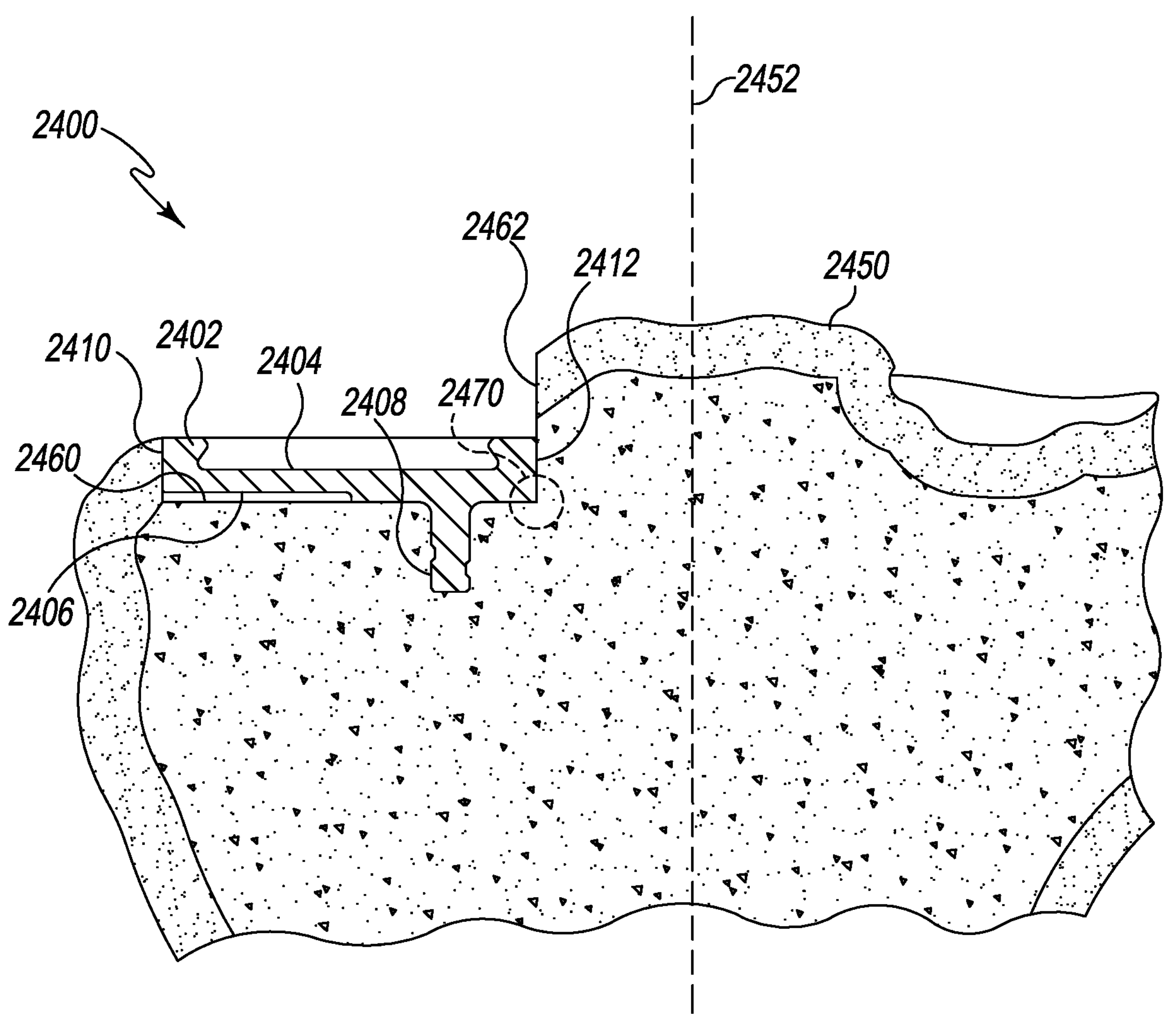
FIG. 24 is a cross-sectional view of a typical unicondylar tibial tray implanted into a tibia of a patient.

Individual unicondylar knee prostheses are used to replace a single condyle femoral-tibial interface of a patient's knee. For example, a typical unicondylar knee prosthesis 2400 is shown in FIG. 24 having been implanted into a patient's tibia 2450. The unicondylar knee prosthesis 2400 includes a unicondylar tibial tray 2402, which is usually formed from a unitary or monolithic, rigid metallic material such as titanium. The unicondylar tibial tray 2402 includes a top support surface 2404 shaped to support a polymer tibial insert (not shown) during use. The polymer tibial insert is configured to articulate with the patient's corresponding natural or artificial femoral condyle to form the single condyle femoral-tibial interface.

The unicondylar tibial tray 2402 also includes a bottom surface 2406 opposite the top support surface 2404. One or more pegs or keels 2408 may extend distally from the bottom surface 2406 to provide structural support for the unicondylar knee prosthesis 2400 in the patient's tibia 2450. The unicondylar tibial tray 2402 also includes an outboard side 2410 and an inboard side 2412 opposite the outboard side 2410. When the unicondylar knee prosthesis 2400 is implanted into the patient's tibia 2450 as shown in FIG. 24, the inboard side 2412 of the unicondylar tibial tray 2402 is located inwardly toward the anatomical axis 2452 of the patient's tibia 2450, relative to the outboard side 2410.

An orthopaedic surgeon may implant the typical unicondylar knee prosthesis 2400 into the patient's tibia 2450 via a corresponding orthopaedic surgical procedure. Typically, such orthopaedic surgical procedures may include a number of tibial cuts, including a transverse plane cut 2460 and a sagittal plane cut 2462, to prepare the patient's tibia 2450 to receive the unicondylar knee prosthesis 2400. Over the lifespan of the unicondylar knee prosthesis 2400, however, a tibial facture can occur under the sagittal plane cut 2462 in the vicinity identified in FIG. 24 via circle 2470 in some situations. In some cases, the tibial facture can be so severe as to cause complete dislocation of the corresponding unicondylar plateau from the remaining portion of the patient's tibia 2450. Such tibial factures may be caused by the creation of a stress raiser under the sagittal plane cut 2462 in the vicinity of the circle 2470. For example, a stress raiser may be created due to the combination of the rigidity of the unicondylar tibial tray 2402, the relative stiff cortical bone of the exterior of the patient's tibia 2450, and the relative soft cancellous bone of the interior of the patient's tibia 2450, which can cause a lever action to occur with the stiff cortical bone acting as a fulcrum. Under such conditions, the inboard side 2412 of the unicondylar tibial tray 2402 applies additional stress downwardly at the sagittal plane cut 2462, which may result in an associated tibial fracture.

Referring now to FIGS. 1-4, a unicondylar knee prosthesis 100 according to the present disclosure includes a unicondylar insert platform 102 and a tibial base 104 extending distally from the unicondylar insert platform 102.

As discussed in more detail below, the unicondylar insert platform 102 and the tibial base 104 have different stiffness (e.g., different densities or porosity), with the unicondylar insert platform 102 having a stiffness greater than the tibial base 104. For example, in the illustrative embodiment, the unicondylar insert platform 102 is rigid and has a uniform stiffness gradient. That is, the stiffness of the unicondylar insert platform 102 is equal, within typical manufacturing tolerances, at each location or portion of the unicondylar insert platform 102. Conversely, the tibial base 104 has a non-uniform stiffness gradient. That is, the stiffness of the tibial base 104 is different at different locations of the tibial base 104. For example, the tibial base 104 may have a stiffness that decreases in an outboard-to-inboard direction, have an increased stiffness toward the center of the tibial base 104, and/or may have a stiffness gradient that increases or decreases in other directions or otherwise have a cross-section of varying density. As discussed in more detail below, the non-uniform stiffness gradient of the tibial base 104 may reduce the magnitude of any stress raiser occurring at the sagittal plane cut of the patient's tibia and, thereby, decrease the likelihood of tibial fractures in the patient's corresponding tibia.

It should be appreciated that the stiffness of tibial base 104 may be controlled or defined by controlling various aspects of the tibial base 104. For example, in the illustrative embodiments described below, the stiffness of the tibial base 104 is controlled by controlling the density of the tibial base 104. As such, a particular stiffness gradient of the tibial base 104 may be defined by establishing a particular density (or porosity) gradient of the tibial base 104. Of course, in other embodiments, other methodologies for controlling the stiffness of the tibial base 104 may be used in other embodiments, such as forming the tibial base 104 from different materials. As such, although a particular embodiment may be described below with regard to the density of the tibial base 104, it should be appreciated that such embodiments are equally applicable to characteristics of the tibia base 104 that affect its stiffness.

As shown in FIGS. 1-4, each of the unicondylar insert platform 102 and the tibial base 104 has a similar, generally "D"-shaped top profile. The unicondylar insert platform 102 includes a top surface 110 and a bottom surface 112 opposite the top surface 110. The top surface 110 is configured to receive and support an associated unicondylar tibial insert (not shown). As shown best in FIG. 1, the unicondylar insert platform 102 may also include a railing 114, which is configured to capture a portion of the associated unicondylar tibial insert to secure the tibial insert to the unicondylar insert platform 102 and, in some embodiments, allow some motion of the unicondylar tibial insert on the top surface 110. The unicondylar insert platform 102 may be formed from any suitable rigid material capable of supporting the associated unicondylar tibial insert during use. For example, in the illustrative embodiment, the unicondylar insert platform 102 is formed from a titanium material, a cobalt chromium material, a ceramic material, a polymer material, and/or the like.

Similar to the unicondylar insert platform 102, the tibial base 104 includes a top surface 120 and a bottom surface 122 opposite the top surface 120. The top surface 120 is attached or otherwise secured to the bottom surface 112 of the unicondylar insert platform 102. To do so, any suitable securement mechanism or device may be used to secure the unicondylar insert platform 102 and the tibial base 104 together. For example, in some embodiments, the top surface 120 of the tibial base 104 is secured to the bottom surface 112 of the unicondylar insert platform 102 via orthopaedic cement, glue, or the like. In other embodiments, orthopaedic screws or other securement devices may be used. Alternatively, in other embodiments, the tibial base 104 may be integral to the unicondylar insert platform 102 such that the unicondylar insert platform 102 and the tibial base 104 form a unitary construction. For example, the unicondylar insert platform 102 and the tibial base 104 may be manufactured together using a three-dimensional printing process, a milling or machining process, an extrusion process, or other unitary construction manufacturing process. As such, the tibial base 104 may be formed from a material similar to or different from the unicondylar insert platform 102. For example, the tibial base 104 may be formed from a titanium material, a cobalt chromium material, a ceramic material, a polymer material, and/or the like.

Figures 4, 5:
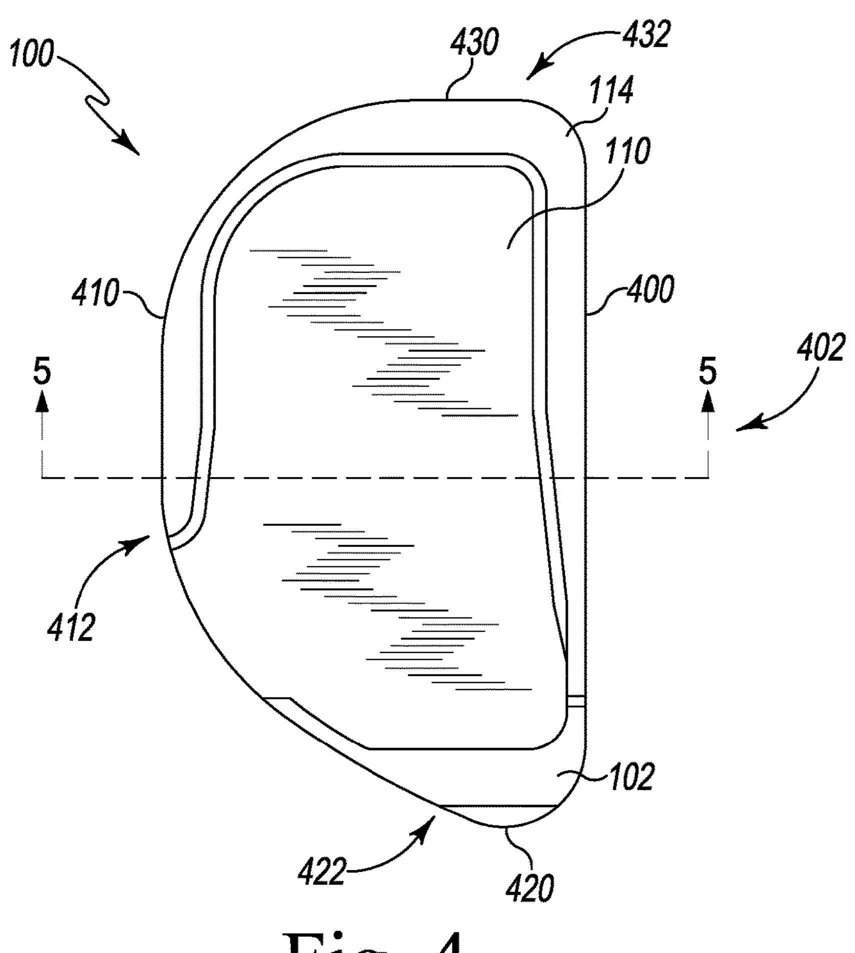
FIG. 4 is a top plan view of the unicondylar knee prosthesis of FIG. 1.
FIG. 5 is a cross-sectional elevation view taken generally along a coronal cross-section line 5-5 of FIG. 4.

As best shown in FIG. 4, the tibial base 104 includes a generally straight side surface 400 that defines an inboard side 402, a generally curved side surface 410 that defines an outboard side 412 opposite the inboard side 402, an end surface 420 that defines an anterior side 422, and an end surface 430 that defines a posterior side 432 of the tibial base 104. When the unicondylar knee prosthesis 100 is implanted into the patient's tibia, the inboard side 402 of the tibial base 104 is located toward the anatomical axis of the patient's corresponding tibia. For example, the illustrative unicondylar knee prosthesis 100 may be used to replace the patient's medial condyle of the patient's left knee or the lateral condyle of the patient's right knee. However, it should be appreciated that the concepts described herein are equally applicable to a unicondylar knee prosthesis configured to replace the lateral condyle of the patient's left knee or the medial condyle of the patient's right knee.

Figure 3:
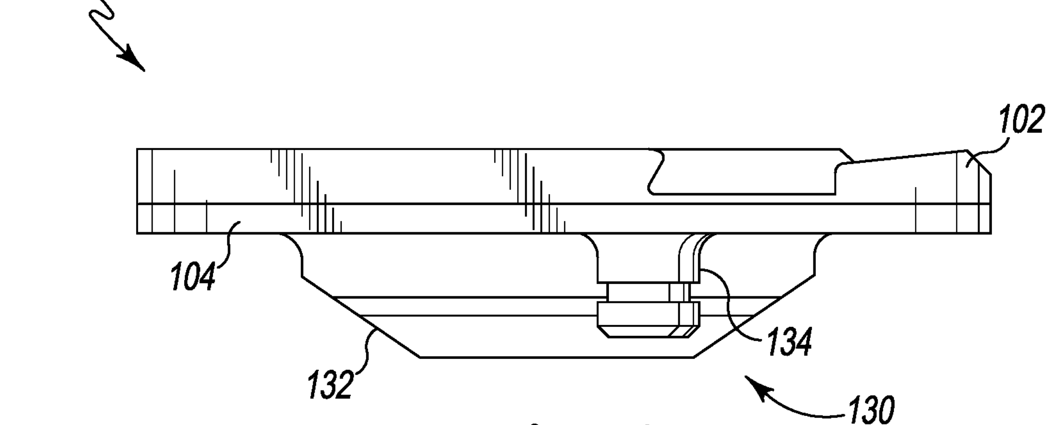
FIG. 3 is an outboard side elevation view of the unicondylar knee prosthesis of FIG. 1.

The tibial base 104 is configured to be coupled to a surgically-prepared surface of the proximal end of a patient's tibia (not shown) as described in more detail below. To facilitate securement to the patient's tibia, the tibial base 104 may include one or more anchoring devices 130. For example, as best shown in FIG. 3, the tibial base 104 may include one or more keels 132 and/or one or more pegs 134, which extend distally from the bottom surface 122 of the tibial base. When the tibial base 104 is coupled to the patient's tibia, the anchoring devices 130 are embedded in the patient's tibia to thereby secure the unicondylar knee prosthesis 100 to the patient's corresponding bony anatomy.

Referring now to FIG. 5, as discussed above, the unicondylar insert platform 102 has a stiffness greater than the tibial base 104. For example, the tibial base 104 may have a stiffness (e.g., a density or porosity), relative to the unicondylar insert platform 102, that is less than 50% of the stiffness of the unicondylar insert platform 102, less than 40% of the stiffness of the unicondylar insert platform 102, less than 30% of the stiffness of the unicondylar insert platform 102, less than 20% of the stiffness of the unicondylar insert platform 102, or less than 10% of the stiffness of the unicondylar insert platform 102, depending on various criteria such as the bony anatomy of the patient (e.g., the corresponding stiffness or density of the patient's bone). For example, the unicondylar insert platform 102 may be formed from a solid material (e.g., solid titanium, cobalt chromium, etc.) material and have a stiffness (e.g., a Young's modulus) of 100 gigapascals or greater. Conversely, the tibial base 104 is formed to have a stiffness of less than about 50 gigapascals, less than 40 gigapascals, less than 30 gigapascals, less than 20 gigapascals, or less than 10 gigapascals in some embodiments. In one particular embodiment, the tibia base 104 may have a stiffness of around 2 gigapascals.

It should be appreciated that the unicondylar insert platform 102 provides a support surface for the associated unicondylar tibial insert, while the tibial base 104 provides support for the unicondylar insert platform 102 and structure for anchoring the unicondylar knee prosthesis 100 into the patient's tibia. As such, as shown in FIG. 5, the unicondylar insert platform 102 may be have a thickness 500 less than a thickness 502 (ignoring the length of any keel 132 or peg 134) of the tibial base 104. For example, the unicondylar insert platform 102 may have a thickness 500 that is less than 50%, 25%, or less than the thickness 502 of the tibial base 104.

In the illustrative embodiment of FIG. 5, the tibial base 104 is shown as having a uniform stiffness (e.g., density or porosity) that is less than the stiffness (e.g., density or porosity) of the unicondylar insert platform 102. However, in other embodiments as discussed below, the tibial base 104 may have a non-uniform stiffness gradient. That is, the stiffness (e.g., density or porosity) of the tibial base 104, while being less than the stiffness (e.g., density or porosity) of the unicondylar insert platform 102, may vary across the tibial base 104. For example, the stiffness (e.g., density or porosity) of the tibial base 104 may increase or decrease in the outboard-to-inboard direction and/or in anterior-to-posterior direction. In some embodiments, the stiffness (e.g., density or porosity) of the tibial base 104 may increase in a particular direction (e.g., the outboard-to-inboard direction) to a location of high density and then decrease again in the same direction so as to form an offset (e.g., central) area of high density. Additionally, in some embodiments, the tibial base 104 may have a stiffness (e.g., density or porosity) gradient that is non-uniform in one direction but uniform in another direction. For example, the tibial base 104 may have a non-uniform stiffness (e.g., density or porosity) gradient in the outboard-to-inboard direction (i.e., across a coronal cross-section) while having a uniform density gradient in the anterior-to-posterior direction (i.e., across a sagittal cross-section).

As discussed above, in the illustrative embodiments described below, the stiffness of the tibial base 104 is controlled by controlling the density of the tibial base 104. However, again, it should be appreciated that other characteristics of the tibial base 104 (e.g., porosity) may be controlled to control its stiffness.

Figures 6, 7, 8, 9:
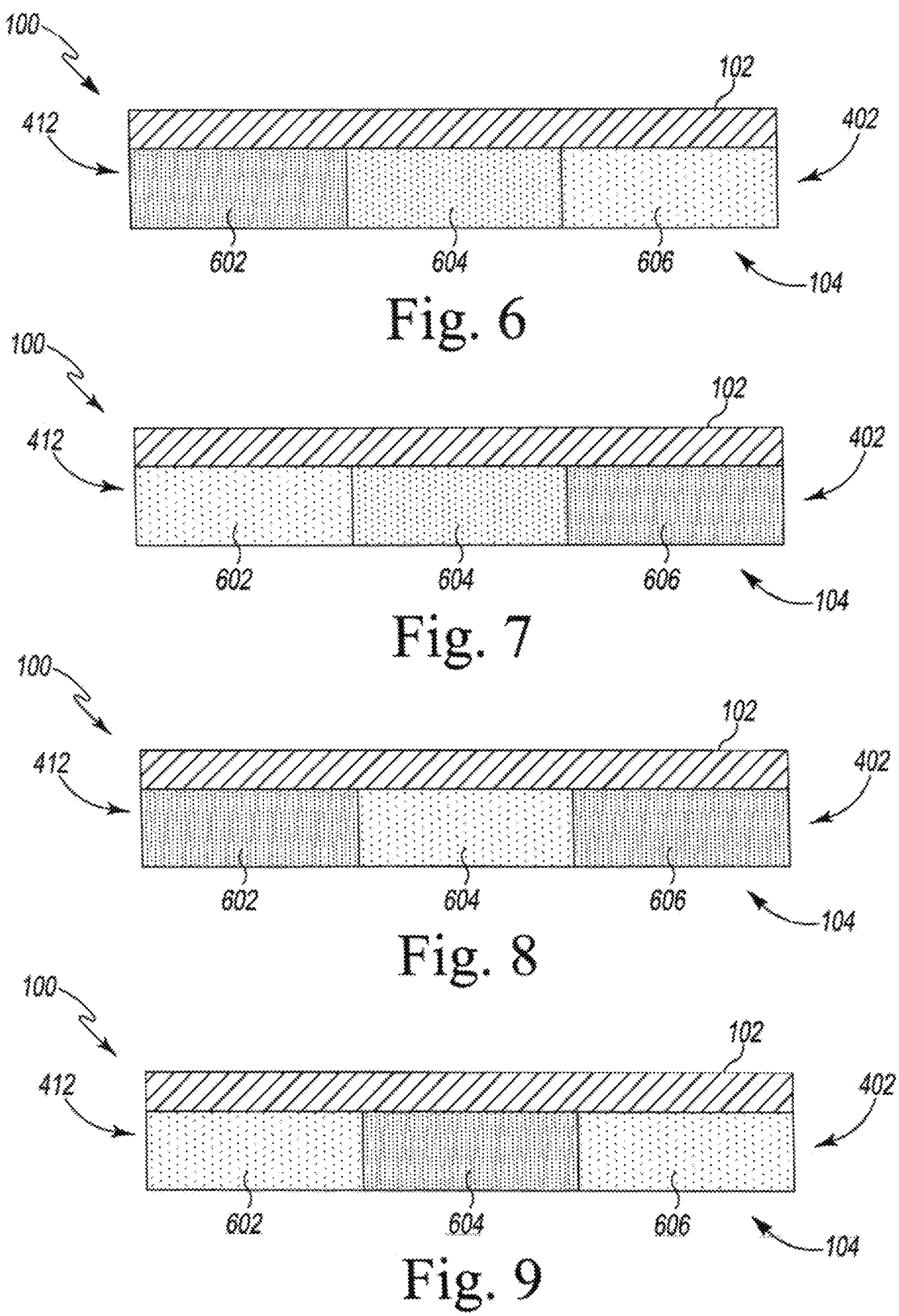
FIG. 6 is a coronal cross-sectional elevation view of another embodiment of the unicondylar knee prosthesis of FIG. 5 including a tibial base having a non-uniform density gradient formed from distinct sections of varying densities.
FIG. 7 is a coronal cross-sectional elevation view of another embodiment of the unicondylar knee prosthesis of FIG. 5 including a tibial base having a non-uniform density gradient formed from distinct sections of varying densities.
FIG. 8 is a coronal cross-sectional elevation view of another embodiment of the unicondylar knee prosthesis of FIG. 5 including a tibial base having a non-uniform density gradient formed from distinct sections of varying densities.
FIG. 9 is a coronal cross-sectional elevation view of another embodiment of the unicondylar knee prosthesis of FIG. 5 including a tibial base having a non-uniform density gradient formed from distinct sections of varying densities.

Referring now to FIGS. 6-9, in some embodiments, the non-uniform density gradient of the tibial base 104 may be defined by multiple discrete sections of uniform density or by a gradually changing density. For example, the tibial base 104 may include or otherwise be defined by multiple sections 602, 604, 606 when viewed in a cross-sectional coronal plane. Each section 602, 604, 606 extends in the anterior-to-posterior direction and has a corresponding uniform density that is different from each other section 602, 604, 606 and/or different from each adjacent section 602, 604, 606. For example, as shown in FIG. 6, the tibial base 104 may include an outboard-most section 602 having a relative high density (e.g., a density, p, that is about 50% of the density of the unicondylar insert platform 102 or otherwise having a stiffness of about 20 gigapascals), a central section 604 having a relative moderate density (e.g., a density, p, that is about 50% of the density of the unicondylar insert platform 102 or otherwise having a stiffness of about 5 gigapascals), and an inboard-most section 606 having a relative low density (e.g., a density, p, that is about 20% of the density of the unicondylar insert platform 102 or otherwise having a stiffness of about 2 gigapascals), all relative to each other. In the illustrative embodiment of FIG. 6, the inboard-most section 606 has the lowest density of each of the sections that forms the tibial base 104. It should be appreciated that the lower density of the tibial base 104, including on the inboard side 402 of the tibial base 104, relative to a typical, rigid unicondylar knee prosthesis allows the tibial base 104 to flex somewhat during use, which may reduce the likelihood and/or magnitude of any stress raiser occurring at the sagittal plane cut of the patient's tibia. As such, the occurrence of tibial fractures may be reduced with the use of the unicondylar knee prosthesis 100.

In other embodiments, the tibial base 104 may include sections having different density profiles relative to the embodiment of FIG. 6 that also reduce the likelihood and/or magnitude of any stress raiser occurring at the sagittal plane cut of the patient's tibia. For example, in another embodiment shown in FIG. 7, the tibial base 104 may include an outboard-most section 602 having a relative low density (e.g., a density, p, that is about 20% of the density of the unicondylar insert platform 102 or otherwise having a stiffness of about 2 gigapascals), a central section 604 having a relative moderate density (e.g., a density, p, that is about 30% of the density of the unicondylar insert platform 102 or otherwise having a stiffness of about 5 gigapascals), and an inboard-most section 606 having a relative high density (e.g., a density, p, that is about 50% of the density of the unicondylar insert platform 102 or otherwise having a stiffness of about 20 gigapascals), all relative to each other.

Additionally, in another embodiment shown in FIG. 8, the tibial base 104 may include an outboard-most section 602 having a relative high density (e.g., a density, p, that is about 50% of the density of the unicondylar insert platform 102 or otherwise having a stiffness of about 20 gigapascals), a central section 604 having a relative low density (e.g., a density, p, that is about 50% of the density of the unicondylar insert platform 102 or otherwise having a stiffness of about 2 gigapascals), and an inboard-most section 606 having a relative high density (e.g., a density, p, that is about 50% of the density of the unicondylar insert platform 102 or otherwise having a stiffness of about 20 gigapascals), all relative to each other. Further, in another embodiment shown in FIG. 9, the tibial base 104 may include an outboard-most section 602 having a relative low density (e.g., a density, p, that is about 20% of the density of the unicondylar insert platform 102 or otherwise having a stiffness of about 2 gigapascals), a central section 604 having a relative high density (e.g., a density, p, that is about 50% of the density of the unicondylar insert platform 102 or otherwise having a stiffness of about 20 gigapascals), and an inboard-most section 606 having a relative low density (e.g., a density, p, that is about 20% of the density of the unicondylar insert platform 102 or otherwise having a stiffness of about 2 gigapascals), all relative to each other.

It should also be appreciated that although the embodiments of the tibial base 104 of FIGS. 6-9 are shown as having only three sections, the tibial base 104 may include additional or few sections in other embodiments. For example, in some embodiments, the tibial base 104 may include a larger number of sections (e.g., five or more discrete sections of uniform density) that approximate a gradual change in density (or stiffness) of the tibial base 104 in the outboard-to-inboard direction (i.e., across the coronal plane).

Figures 10, 11, 12, 13:
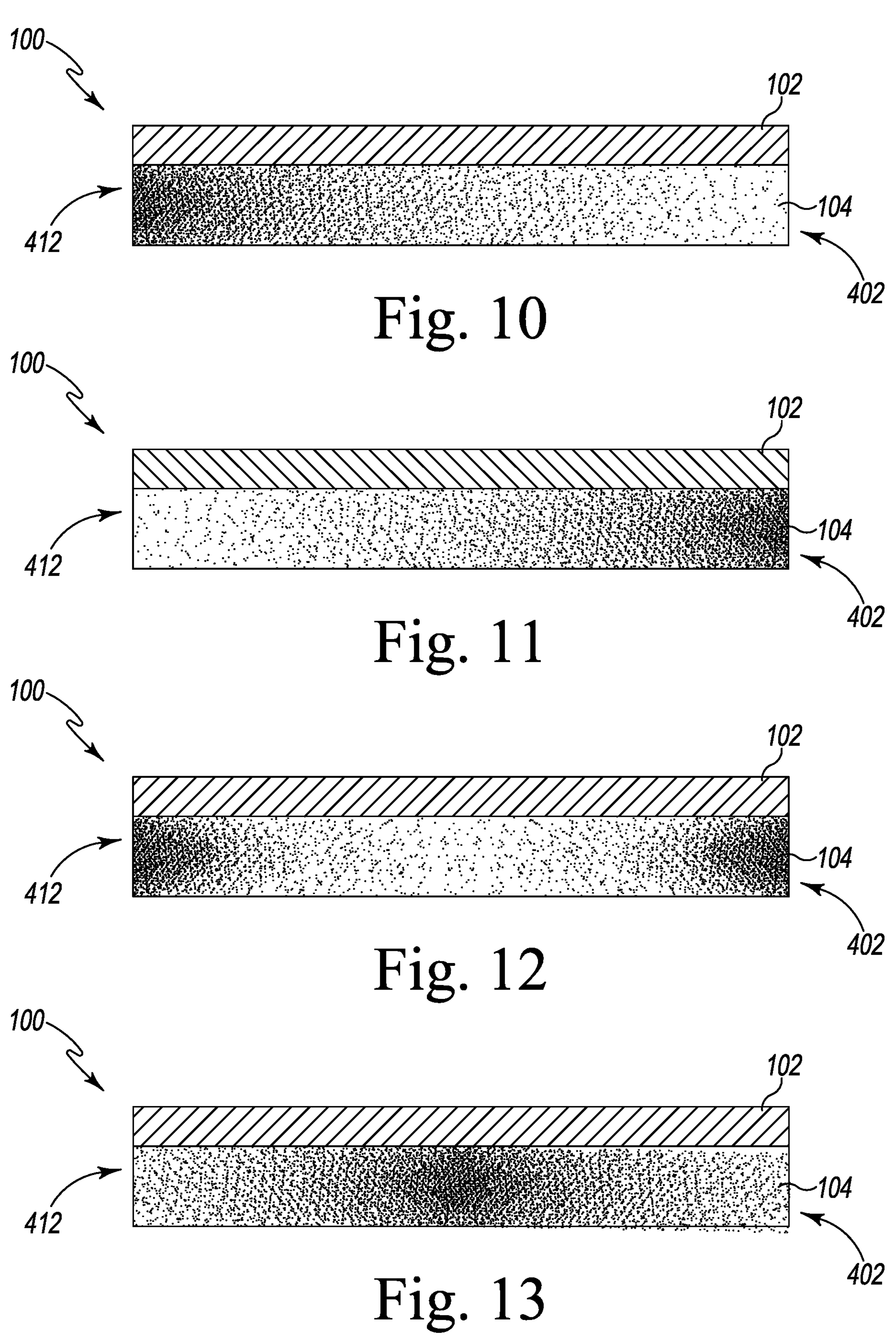
FIG. 10 is a coronal cross-sectional elevation view of another embodiment of the unicondylar knee prosthesis of FIG. 5 including a tibial base having a non-uniform density gradient formed from a gradually varying density.
FIG. 11 is a coronal cross-sectional elevation view of another embodiment of the unicondylar knee prosthesis of FIG. 5 including a tibial base having a non-uniform density gradient formed from a gradually varying density.
FIG. 12 is a coronal cross-sectional elevation view of another embodiment of the unicondylar knee prosthesis of FIG. 5 including a tibial base having a non-uniform density gradient formed from a gradually varying density.
FIG. 13 is a coronal cross-sectional elevation view of another embodiment of the unicondylar knee prosthesis of FIG. 5 including a tibial base having a non-uniform density gradient formed from a gradually varying density.

Alternatively, as shown in FIGS. 10-13, the tibial base 104 may have a non-uniform stiffness (e.g., density or porosity) gradient defined by a gradually changing stiffness (e.g., density or porosity) in one or more directions. For example, as shown in FIG. 10, the tibial base 104 may be have a non-uniform density gradient that gradually decreases in the outboard-to-inboard direction from an area of relative high density to an area of relative low density (e.g., from a density of about 20 gigapascals at the outboard side 412 to a density of about 2 gigapascals at the inboard side 402). Additionally, in another embodiment shown in FIG. 11, the tibial base 104 may be have a non-uniform density gradient that gradually increases in the outboard-to-inboard direction from an area of relative low density to an area of relative high density (e.g., from a density of about 2 gigapascals at the outboard side 412 to a density of about 20 gigapascals at the inboard side 402).

Alternatively, in another embodiment shown in FIG. 12, the tibial base 104 may be have a non-uniform density gradient that gradually decreases in the outboard-to-inboard direction from an area of relative high density at the outboard side 412 to a central area of relative low density and then gradually increases in the outboard-to-inboard direction from the central area of relative low density to an area of relative high density at the inboard side 402 (e.g., from a density of about 20 gigapascals at the outboard side 412 to a density of about 2 gigapascals at a central location and then to a density of about 20 gigapascals at the inboard side 402). Further, in another alternative embodiment shown in FIG. 13, the tibial base 104 may be have a non-uniform density gradient that gradually increases in the outboard-to-inboard direction from an area of relative low density at the outboard side 412 to a central area of relative high density and then gradually decreases in the outboard-to-inboard direction from the central area of relative high density to an area of relative low density at the inboard side 402 (e.g., from a density of about 2 gigapascals at the outboard side 412 to a density of about 20 gigapascals at a central location and then to a density of about 2 gigapascals at the inboard side 402).

In each of the embodiments of FIGS. 10-13, the stiffness or density gradient of the tibial base 104 is illustratively uniform in the anterior-to-posterior direction. That is, the density of the tibial base 104 changes in the outboard-to-inboard direction, while remaining relatively uniform in the anterior-to-posterior direction. However, in other embodiments as discussed in more detail below, the stiffness or density of the tibial base 104 may also change in the anterior-to-posterior direction, which may define localized areas of high or low density/stiffness.

Figure 14:
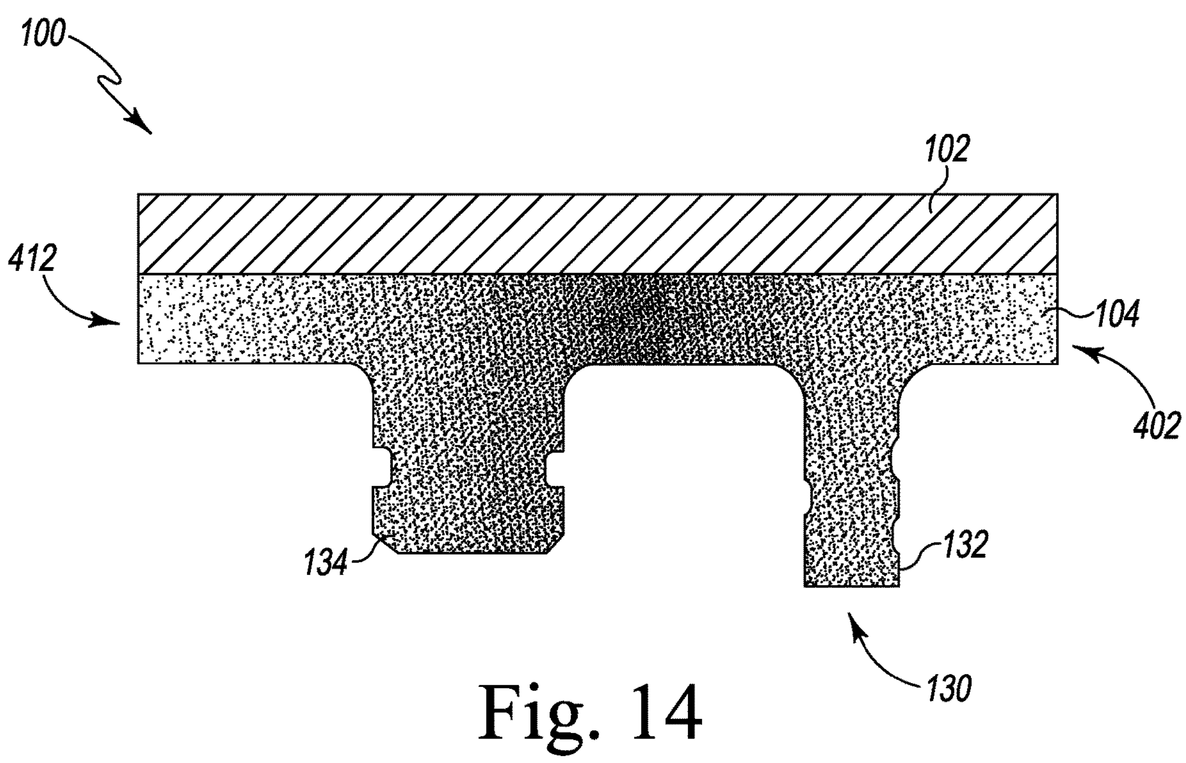
FIG. 14 is a coronal cross-sectional elevation view of another embodiment of the unicondylar knee prosthesis of FIG. 5 including a tibial base having a non-uniform density gradient formed from a gradually varying density and a pair of anchors having a uniform density gradient.
Figure 15:
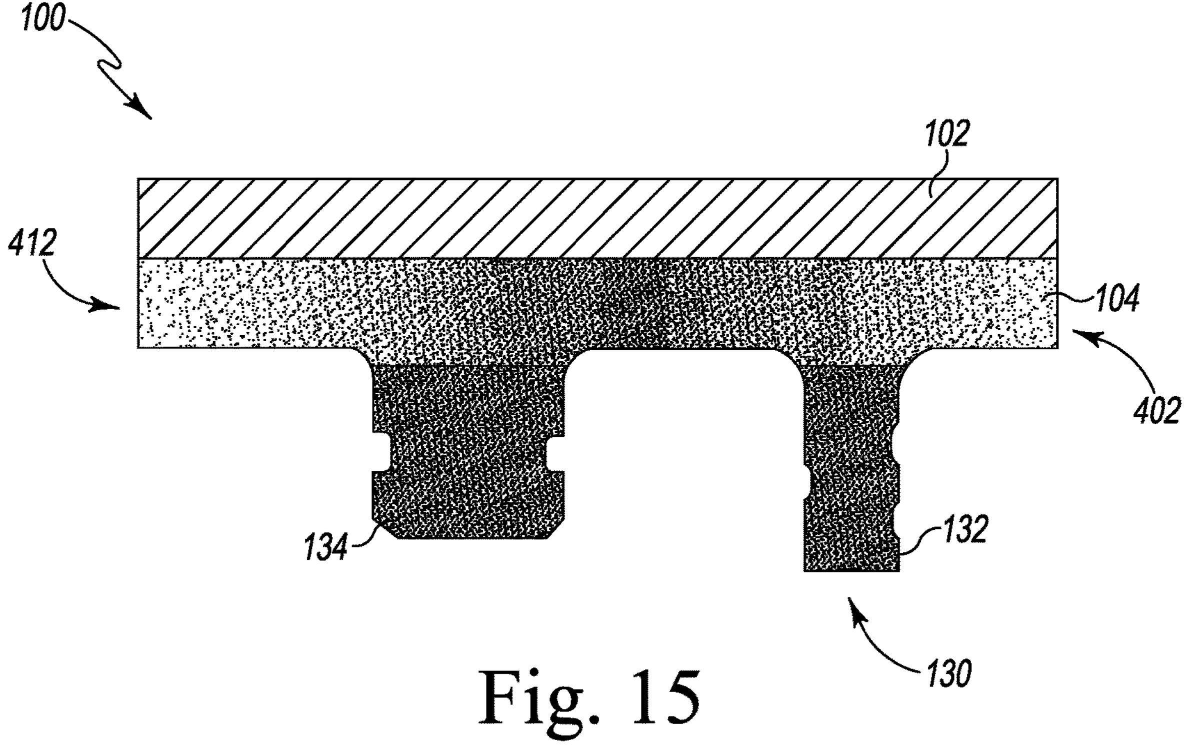
FIG. 15 is a coronal cross-sectional elevation view of another embodiment of the unicondylar knee prosthesis of FIG. 5 including a tibial base having a non-uniform density gradient formed from a gradually varying density and a pair of anchors having a uniform density gradient.

Referring now to FIG. 14, in some embodiments, the stiffness (e.g., density or porosity) of the anchoring devices 130 may vary consistently with the density of the tibial base 104. For example, the density of the anchoring devices 130 may match the density of the tibial base 104 proximal to the particular anchoring device 130. In an illustrative embodiment, as shown in FIG. 14, the density of the peg 134 increases in the outboard-to-inboard direction similar to the portion of the tibial base 104 immediately proximal to the peg 134. Similarly, the density of the keel 132 decreases in the outboard-to-inboard direction similar to the portion of the tibial base 104 immediately proximal to the keel 132. However, in other embodiments, the anchoring devices 130 may have an increased stiffness or density relative to the tibial base 104. For example, as shown in FIG. 15, the keel 132 and the peg 134 may have a relative high density (e.g., a density of about 20 gigapascals or about 50% or greater of the density of the unicondylar insert platform 102) irrespective of the density of the portion of the tibial base 104 immediately proximal to keel 132 and peg 134. It should be appreciated that the increased density of the anchoring devices 130, relative to other portions of the tibial base 104, may improve the securement of the unicondylar knee prosthesis 100 to the patient's corresponding bony anatomy.

Figure 16:
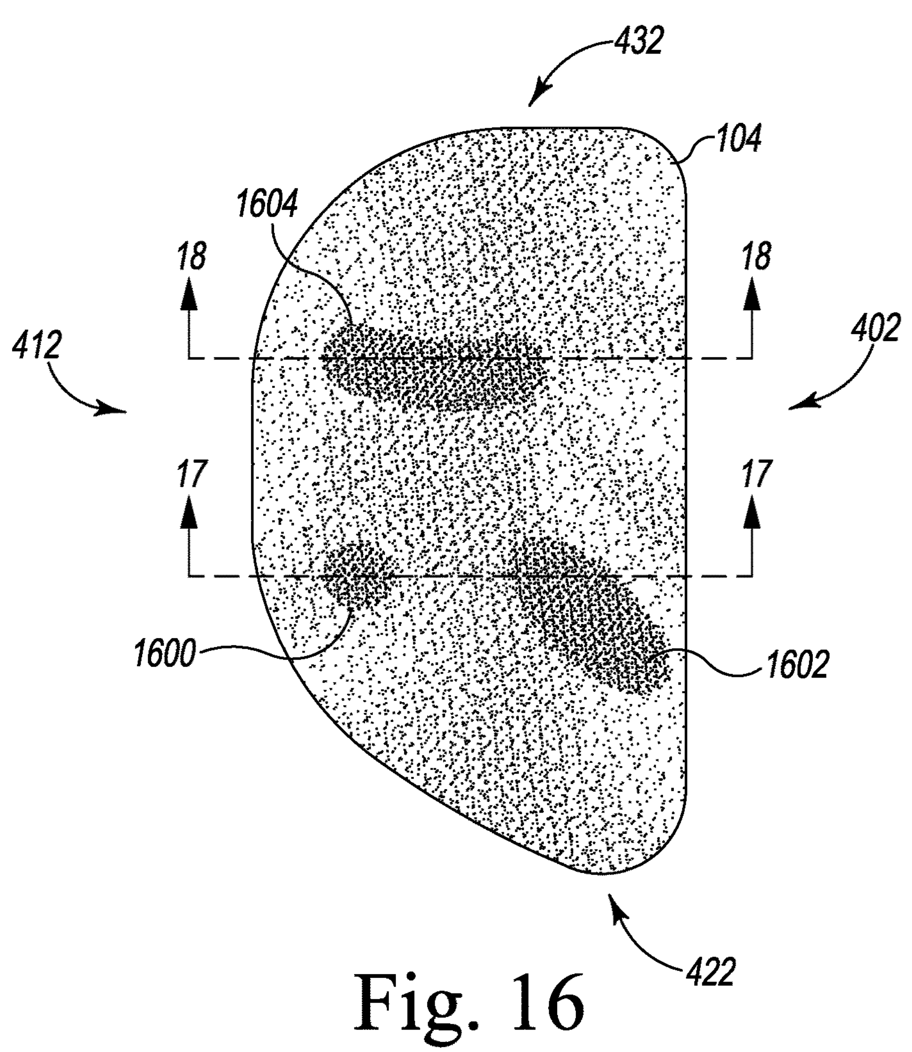
FIG. 16 is a top plan view of another embodiment of the unicondylar knee prosthesis of FIGS. 1-5 including a number of density wells.
Figure 17:
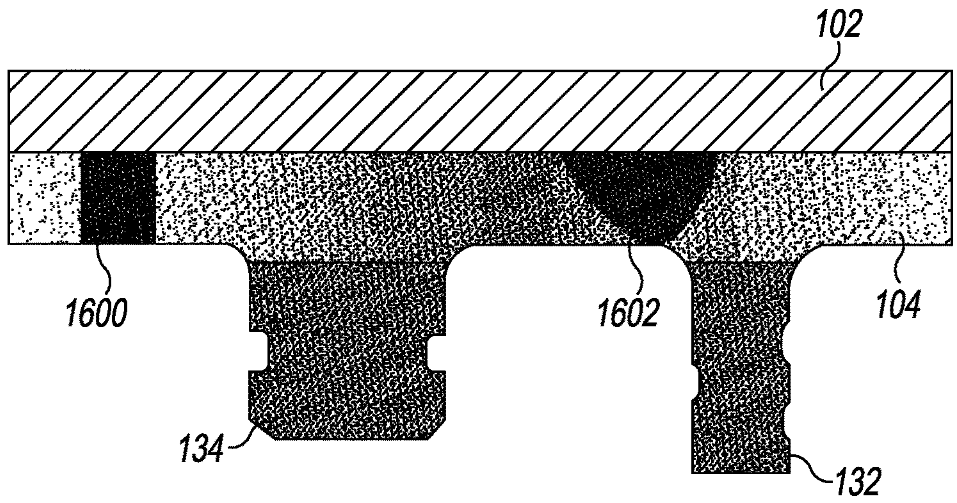
FIG. 17 is a cross-sectional elevation view taken generally along a coronal cross-section line 17-17 of FIG. 16.
Figure 18:
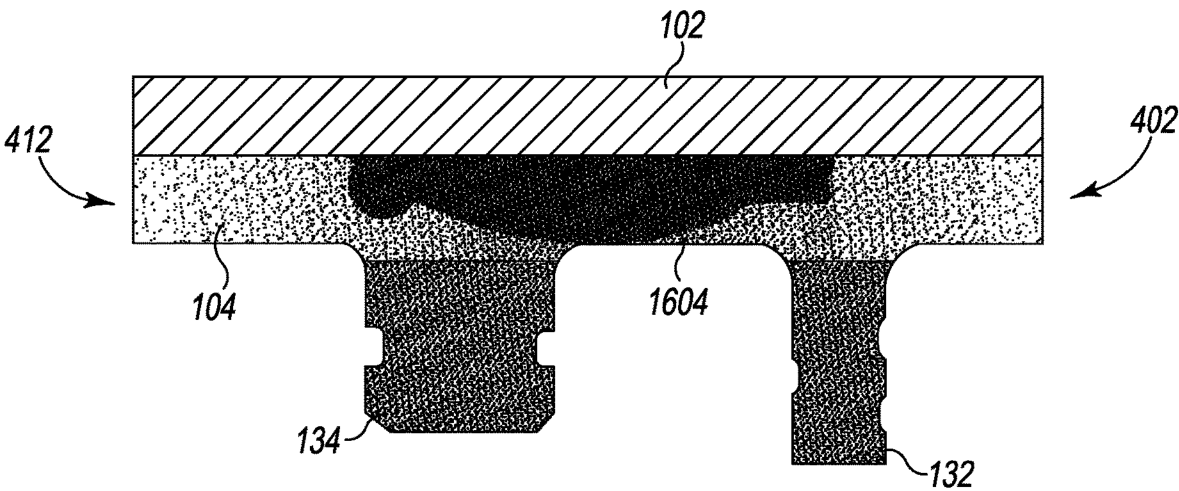
FIG. 18 is a cross-sectional elevation view taken generally along a coronal cross-section line 18-18 of FIG. 16.

As discussed above, in some embodiments, the stiffness (e.g., density or porosity) of the tibial base 104 may be non-uniform in multiple directions (e.g., in the outboard-to-inboard direction, the anterior-to-posterior direction, and/or the inferior-to-superior direction) so as to create or define areas of localized increased or decreased stiffness (e.g., density or porosity). For example, in some embodiments as shown in FIG. 16, the tibial base 104 may include one or more density wells or regions 1600, 1602, 1604. Each of the density wells 1600, 1602, 1604 defines a volume of the tibial base 104 having an increased or decreased density relative to a region of the tibial base 104 immediately adjacent to the corresponding density well 1600, 1602, 1604. Additionally, each of the density wells 1600, 1602, 1604 may have a similar or different two-dimensional and/or three-dimensional shape. For example, the density well 1600 has a circular top profile shape as shown in FIG. 16 and a cylindrical or column coronal cross-sectional shape as shown in FIG. 17. Alternatively, the density well 1602 has an oval top profile shape as shown in FIG. 16 and a parabolic coronal cross-sectional shape as shown in FIG. 17. Of course, the density wells defined in the tibial base 104 may have more complex shapes in other embodiments. For example, the density well 1604 has a curved oblong top profile shape as shown in FIG. 16 and a complex parabolic-like coronal cross-sectional shape as shown in FIG. 18.

As such, it should be appreciated that such density wells may have any suitable geometrical or complex top profile and/or cross-sectional shape, including linear sidewalls (e.g., density well 1600) or non-linear or curved sidewalls (e.g., density well 1602). The location and shape of such density wells may be based on the bony anatomy of the patient (e.g., the patient's tibia), the particular orthopaedic surgical procedure to be performed, preferences of the orthopaedic surgeon, and/or other criteria. Additionally, it should be appreciated that while the density wells 1600, 1602, 1604 define localized areas of increased or decreased density, the tibial base 104 may have an overall non-uniform density gradient. For example, as shown in FIG. 16, the tibial base 104 includes a density gradient that is non-uniform in the outboard-to-inboard direction (similar to the tibial base 104 of FIG. 13) and uniform in the anterior-to-posterior direction, while also including the density wells 1600, 1602, 1604.

Figure 19:
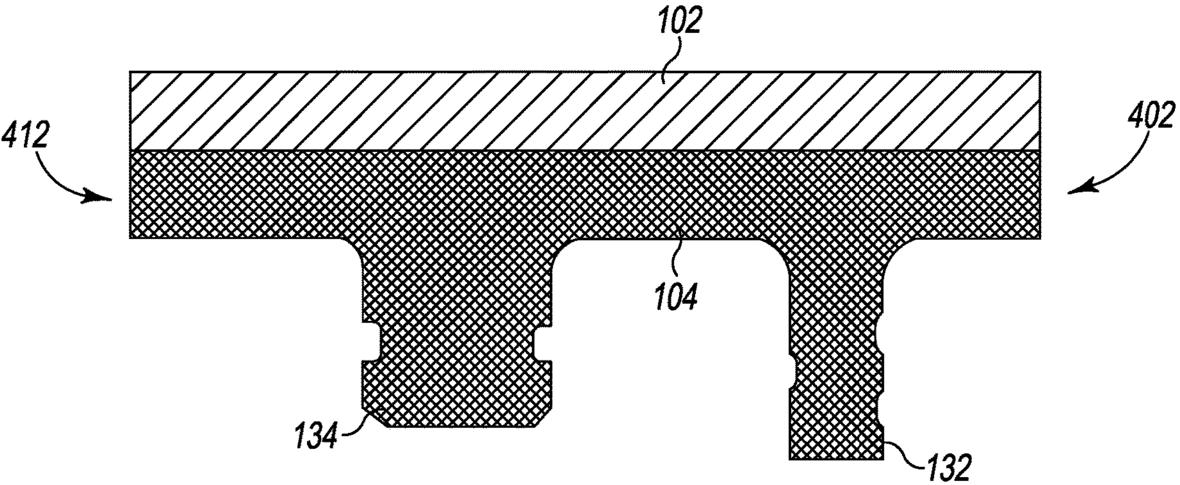
FIG. 19 is a coronal cross-sectional elevation view of another embodiment of the unicondylar knee prosthesis of FIG. 5 including a tibial base formed from a Body-Centered Cubic (BCC) lattice structure and having a non-uniform density gradient.

Referring now to FIG. 19, as discussed above, the tibial base 104 may be formed or fabricated using any suitable material and manufacturing process. For example, in some embodiments as illustrated in FIG. 19, the tibial base 104 is formed from a lattice structure, such as a Body-Centered Cubic (BCC) lattice structure. Of course, in other embodiments other types of lattice structures may be used to control the stiffness (e.g., density or porosity of the tibial base 104). Regardless, in such embodiments, the lattice structure of the tibial base 104, as well as the rigid unicondylar insert platform 102, may be formed via a three-dimensional (3D) printing process or similar manufacturing process. It should be appreciated that the fabrication of the tibial base 104 from a lattice structure, such as a BCC lattice structure, allows the formation of a tibial base 104 having a non-uniform density gradient, such as those illustrated and described above in regard to FIGS. 5-18. However, it should be appreciated that the tibial base 104, as well as the unicondylar insert platform 102, may be formed from other manufacturing processes in other embodiments.

Referring now to FIGS. 20 and 21, in some embodiments, the stiffness (e.g., density or porosity) of the tibial base 104 may be controlled or otherwise defined mechanically manipulating the tibial base 104. For example, as shown in FIG. 20, the stiffness (e.g., density or porosity) of the tibial base 104 may be controlled by forming, machining, or otherwise establishing a number of apertures 2000 in the tibial base 104. By controlling the number and/or proximity of the apertures 2000, the stiffness (e.g., density or porosity) of the tibial base 104 may be controlled. In the illustrative embodiment of FIG. 20, the non-uniform stiffness gradient of the tibial base 104 is be defined by multiple discrete sections of uniform stiffness (e.g., density or porosity) or by a gradually changing stiffness (e.g., density or porosity). To do so, the illustrative tibial base 104 includes or is otherwise defined by multiple sections 2002, 2004, 2006 when viewed in a cross-sectional coronal plane. Each section 2002, 2004, 2006 extends in the anterior-to-posterior direction and has a corresponding uniform density that is different from each other section 2002, 2004, 2006 and/or different from each adjacent section 2002, 2004, 2006. For example, as shown in FIG. 20, the tibial base 104 has an outboard-most section 2002 having a relative low number of apertures 2000 and, as such, a lower stiffness or density (e.g., a density, p, that is about 20% of the density of the unicondylar insert platform 102 (not shown in FIG. 20 for clarity) or otherwise having a stiffness of about 2 gigapascals), a central section 2004 having a relative number of apertures 2000 and, as such, a higher stiffness or density (e.g., a density, p, that is about 50% of the density of the unicondylar insert platform 102 (not shown in FIG. 20 for clarity) or otherwise having a stiffness of about 20 gigapascals), and an inboard-most section 2006 having a relative low number of apertures 2000 and, as such, a lower stiffness or density (e.g., a density, p, that is about 20% of the density of the unicondylar insert platform 102 (not shown in FIG. 20 for clarity) or otherwise having a stiffness of about 2 gigapascals), all relative to each other.

Alternatively, in other embodiments as shown in FIG. 21, the stiffness (e.g., density or porosity) of the tibial base may be controlled by forming, machining, or otherwise establishing a number of slots 2100 in the tibial base 104 (shown in FIG. 21 as solid vertical lines). By controlling the number and/or proximity of the slots 2100, the stiffness (e.g., density or porosity) of the tibial base 104 may be controlled. Similar to the embodiment of FIG. 20, in the illustrative embodiment of FIG. 21, the non-uniform stiffness gradient of the tibial base 104 is be defined by multiple discrete sections of uniform stiffness (e.g., density or porosity) or by a gradually changing stiffness (e.g., density or porosity). To do so, the illustrative tibial base 104 includes or is otherwise defined by multiple sections 2102, 2104, 2106 when viewed in a cross-sectional coronal plane. Each section 2102, 2104, 2106 extends in the anterior-to-posterior direction and has a corresponding uniform density that is different from each other section 2102, 2104, 2106 and/or different from each adjacent section 2102, 2104, 2106. For example, as shown in FIG. 21, the tibial base 104 has an outboard-most section 2102 having a relative low number of slots 2100 and, as such, a lower stiffness or density (e.g., a density, p, that is about 20% of the density of the unicondylar insert platform 102 or otherwise having a stiffness of about 2 gigapascals), a central section 2104 having a relative number of slots 2100 and, as such, a higher stiffness or density (e.g., a density, p, that is about 50% of the density of the unicondylar insert platform 102 or otherwise having a stiffness of about 20 gigapascals), and an inboard-most section 2106 having a relative low number of slots 2100 and, as such, a lower stiffness or density (e.g., a density, p, that is about 20% of the density of the unicondylar insert platform 102 or otherwise having a stiffness of about 2 gigapascals), all relative to each other.

Referring now to FIG. 22, in some embodiments, the stiffness (e.g., density or porosity) of the tibial base 104 may be formed or otherwise defined to match the stiffness or density of the patient's corresponding bone. For example, the tibial base 104 may be formed to have an increased density in those areas contacting or otherwise overlaying the patient's cortical bone, while having a lower density in those areas contacting or otherwise overlying the patient's cancellous bone. For example, as shown in FIG. 22, the tibial base 104 may include a rim 2202 having a relative high stiffness or density (e.g., a density, p, that is about 50% of the density of the unicondylar insert platform 102 (not shown in FIG. 20 for clarity) or otherwise having a stiffness of about 20 gigapascals) to match the patient's relatively stiff cortical tibial bone. The remaining portion 2204 of the tibial base 104, which covers the patent's cancellous tibial bone, may have relative low stiffness or density (e.g., a density, p, that is about 20% of the density of the unicondylar insert platform 102 (not shown in FIG. 20 for clarity) or otherwise having a stiffness of about 2 gigapascals). Of course, in other embodiments, the stiffness (e.g., density or porosity) of the portion of the tibial base covering or overlaying the patients cancellous bone may have a non-uniform stiffness (e.g., density or porosity) as described above.

Referring now to FIG. 23, in some embodiments, the unicondylar knee prosthesis 100 may be fabricated using a manufacturing method 2300. The method 2300 begins with block 2302 in which the desired stiffness gradient (e.g., density or porosity gradient) or profile of the tibial base 104 of the unicondylar knee prosthesis 100 is determined. For example, in block 2304, the stiffness gradient (e.g., density or porosity gradient) of the tibial base 104 may be determined based on the patient's bony anatomy. In doing so, the stiffness gradient (e.g., density or porosity gradient) or profile of the tibial base 104 may be designed for a particular patient to thereby reduce the likelihood of occurrence and/or magnitude of a stress raiser at the sagittal plane cut of the patient's tibia. In some cases, the stiffness gradient (e.g., density or porosity gradient) may be based on the corresponding stiffness, density, or state of the patient's tibia, which may be determined or identified via associated medical images (e.g., X-ray images, computed tomography (CT) scan images, magnetic resonance imaging (MRI) images, etc.). For example, the shape, size, and location of one or more density wells of the tibial base 104 may be determined based on the condition or state of the patient's tibia.

In block 2306, the tibial base 104 is fabricated based on the determined stiffness gradient (e.g., density or porosity gradient). For example, in some embodiments, the tibial base 104 is 3D printed in block 2308. Additionally, in some embodiments, the tibial base 104 is formed from a lattice structure, such as a BBC lattice structure as discussed above, in block 2310.

Subsequently, in block 2312, the tibial base 104 is attached to the unicondylar insert platform 102 to form the unicondylar knee prosthesis 100. To do so, as discussed above, the top surface 120 of the tibial base 104 may be secured to the bottom surface 112 of the unicondylar insert platform 102 via orthopaedic cement, glue, or other adhesive. In other embodiments, orthopaedic screws or the like may be used to secure the tibial base 104 to the unicondylar insert platform 102. Alternatively, in other embodiments, the tibial base 104 may be integral to the unicondylar insert platform 102 such that the unicondylar insert platform 102 and the tibial base 104 form a unitary construction. In such embodiments, block 2312 may be skipped and the unicondylar insert platform 102 and the tibial base 104 may be formed together in block 2306 using a 3D printing process, a milling or machining process, an extrusion process, or other unitary construction manufacturing process.

While the disclosure has been illustrated and described in detail in the drawings and foregoing description, such an illustration and description is to be considered as illustrative and not restrictive in character, it being understood that only illustrative embodiments have been shown and described and that all changes and modifications that come within the spirit of the disclosure are desired to be protected.

There are a plurality of advantages of the present disclosure arising from the various features of the methods, apparatuses, and systems described herein. It will be noted that alternative embodiments of the methods, apparatuses, and systems of the present disclosure may not include all of the features described yet still benefit from at least some of the advantages of such features. Those of ordinary skill in the art may readily devise their own implementations of the methods, apparatuses, and systems that incorporate one or more of the features of the present invention and fall within the spirit and scope of the present disclosure as defined by the appended claims.

The invention claimed is:

1. A unicondylar knee prosthesis comprising:

a unicondylar insert platform having a top surface configured to support a unicondylar tibial insert and a bottom surface opposite the top surface, wherein the unicondylar insert platform has a substantially uniform stiffness gradient;

a tibial base attached to the bottom surface of the unicondylar insert platform and extending distally therefrom, wherein the tibial base is configured to be secured to a surgically-prepared proximal end of a patient's tibia and includes a straight inboard side configured to abut a sagittal plane cut of the patent's tibia when the tibial base is secured to the proximal end of the patient's tibia and a curved outboard side opposite the straight inboard side, wherein the tibial base is defined by multiple sections when viewed from the cross-sectional coronal plane and each section has a uniform stiffness that is different from each other section, and wherein the multiple sections includes an inboard-most section that includes the straight inboard side, an outboard-most section that includes the curved outboard side, and at least one central section located between the inboard-most section and the outboard-most section, wherein the inboard-most section has the least stiffness of the multiple sections, the outboard-most section has the greatest stiffness of the multiple sections, and the at least one central section has a stiffness between the stiffness of the inboard-most section and the outboard-most section, and wherein the stiffness of the inboard-most section, the outboard-most section, and the at least one central section are configured to reduce a magnitude of a stress riser occurring at the sagittal plane cut of the patient's tibia when the tibial base is secured to the proximal end of the patient's tibia.

2. The unicondylar knee prosthesis of claim 1, wherein the unicondylar insert platform has a stiffness that is greater than a stiffness of any portion of the tibial base.

3. The unicondylar knee prosthesis of claim 1, wherein tibial base has an anterior side and a posterior side opposite the anterior side, and wherein the stiffness gradient of the tibial base is non-uniform in an anterior-posterior direction.

4. The unicondylar knee prosthesis of claim 1, wherein the stiffness gradient of the tibial base is a density gradient that increases in density from a low density area located toward the inboard side of the tibial base to a high density area, relative to the low density area, located toward the outboard side of the tibial base.

5. The unicondylar knee prosthesis of claim 1, wherein the stiffness gradient of the tibial base is also non-uniform in a proximal-distal direction.

6. The unicondylar knee prosthesis of claim 1, wherein the tibial base comprises a density well, wherein the density well defines a volume of the tibial base having an increased density relative to a region of the tibial base adjacent to the density well.

7. The unicondylar knee prosthesis of claim 6, wherein the density well has a non-uniform density gradient in an inboard- outboard direction and a proximal-distal direction.

8. The unicondylar knee prosthesis of claim 6, wherein the density well is defined by an outer edge adjacent the region of the tibial base, and wherein the outer edge is non-linear when the tibial base is viewed from the cross-sectional coronal plane.

9. The unicondylar knee prosthesis of claim 1, wherein the unicondylar insert platform is formed from a titanium material and the tibial base is formed from a Body-Centered Cubic (BCC) lattice structure.

10. A unicondylar knee prosthesis comprising:

a polymer unicondylar tibial insert; and a unicondylar tibial tray comprising:

a unicondylar insert platform having a top surface configured to support the polymer unicondylar tibial insert and a bottom surface opposite the top surface, wherein the unicondylar insert platform is formed from a titanium material and has a substantially uniform stiffness gradient, and a tibial base attached to the bottom surface of the unicondylar insert platform and extending distally therefrom, wherein the tibial base is configured to be secured to a surgically-prepared proximal end of a patient's tibia and includes a straight inboard side configured to abut a sagittal plane cut of the patent's tibia when the tibial base is secured to the proximal end of the patient's tibia and a curved outboard side opposite the straight inboard side, wherein the tibial base is formed from a Body-Centered Cubic (BCC) lattice structure and is defined by multiple sections when viewed from the cross-sectional coronal plane and each section has a uniform stiffness that is different from each other section, and wherein the multiple sections includes an inboard-most section that includes the straight inboard side, an outboard-most section that includes the curved outboard side, and at least one central section located between the inboard-most section and the outboard-most section, wherein the inboard-most section has the least stiffness of the multiple sections, the outboard-most section has the greatest stiffness of the multiple sections, and the at least one central section has a stiffness between the stiffness of the inboard-most section and the outboard-most section, and wherein the stiffness of the inboard-most section, the outboard-most section, and the at least one central section are configured to reduce a magnitude of a stress riser occurring at the sagittal plane cut of the patient's tibia when the tibial base is secured to the proximal end of the patient's tibia.

11. The unicondylar knee prosthesis of claim 10, wherein tibial base further comprises a plurality of density wells spatially separated from each other, wherein each density well defines a volume of the tibial base having an increased density relative to a region of the tibial base adjacent to the corresponding density well.

12. A method for fabricating a unicondylar knee prosthesis, the method comprising:

determining a non-uniform stiffness gradient for a tibial base of the unicondylar knee prosthesis, wherein the non-uniform stiffness gradient defines a variation in stiffness of the tibial base from an inboard side of the tibial base to an outboard side of the tibial base when viewed from a cross-sectional coronal plane;

fabricating the tibial base based on the determined non-uniform stiffness gradient, wherein the tibial base is configured to be secured to a surgically-prepared proximal end of a patient's tibia and includes a straight inboard side configured to abut a sagittal plane cut of the patent's tibia when the tibial base is secured to the proximal end of the patient's tibia and a curved outboard side opposite the straight inboard side, wherein the tibial base is defined by multiple sections when viewed from the cross-sectional coronal plane and each section has a uniform stiffness that is different from each other section, and wherein the multiple sections includes an inboard-most section that includes the straight inboard side, an outboard-most section that includes the curved outboard side, and at least one central section located between the inboard-most section and the outboard-most section, wherein the inboard- most section has the least stiffness of the multiple sections, the outboard-most section has the greatest stiffness of the multiple sections, and the at least one central section has a stiffness between the stiffness of the inboard-most section and the outboard-most section, and wherein the stiffness of the inboard-most section, the outboard-most section, and the at least one central section are configured to reduce a magnitude of a stress riser occurring at the sagittal plane cut of the patient's tibia when the tibial base is secured to the proximal end of the patient's tibia; and attaching the fabricated tibial base to a bottom surface of a unicondylar insert platform to form the unicondylar knee prosthesis, wherein the unicondylar insert platform includes a top surface configured to support a unicondylar tibial insert and has a substantially uniform stiffness gradient.

13. The method of claim 12, wherein fabricating the tibial base comprises fabricating a Body-Centered Cubic (BCC) lattice structure having the determined non-uniform stiffness gradient.

14. The method of claim 12, wherein determining the non-uniform stiffness gradient comprises determining a non-uniform stiffness gradient for the tibial base that increases in stiffness from a low stiffness area located toward the inboard side of the tibial base to a high stiffness area, relative to the low stiffness area, located toward the outboard side of the tibial base.

15. The unicondylar knee prosthesis of claim 1, wherein the outboard-most section has a stiffness of about 20 gigapascals, the at least one central section has a stiffness of about 5 gigapascals, and the inboard-most section has a stiffness of about 2 gigapascals.

16. The unicondylar knee prosthesis of claim 15, wherein the outboard-most section has a stiffness of about 20 gigapascals, the at least one central section has a stiffness of about 5 gigapascals, and the inboard-most section has a stiffness of about 2 gigapascals.

17. The method of claim 12, wherein fabricating the tibial base comprises:

fabricating the outboard-most section to have a stiffness of about 20 gigapascals;

fabricating the at least one central section to have a stiffness of about 5 gigapascals;

fabricating the inboard-most section to have a stiffness of about 2 gigapascals.

* * * * *